US00PP32137P3

(12) United States Plant Patent
Serrador

(10) Patent No.: US PP32,137 P3
(45) Date of Patent: Sep. 1, 2020

(54) STRAWBERRY PLANT NAMED 'A13-26'

(50) Latin Name: ***Fragaria* x *ananassa* Duch.**
Varietal Denomination: A13-26

(71) Applicant: MASIÁ CISCAR S.A., Lepe (ES)

(72) Inventor: Enrique Masiá Serrador, Lepe (ES)

(73) Assignee: MASIÁ CISCAR S.A., Lepe (ES)

( * ) Notice: Subject to any disclaimer, the term of this patent is extended or adjusted under 35 U.S.C. 154(b) by 0 days.

(21) Appl. No.: 15/932,972

(22) Filed: May 31, 2018

(65) Prior Publication Data

US 2018/0376639 P1 Dec. 27, 2018

Related U.S. Application Data

(60) Provisional application No. 62/604,117, filed on Jun. 22, 2017.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
See application file for complete search history.

(56) References Cited

U.S. PATENT DOCUMENTS

PP26,874 P3 * 6/2016 Vinson ..... A01H 6/7409 Plt./208

* cited by examiner

*Primary Examiner* — Susan McCormick Ewoldt
(74) *Attorney, Agent, or Firm* — Svendsen Legal, LLC

(57) ABSTRACT

A new short-day strawberry plant named 'A13-26' is disclosed, with exceptional yield and flavor characteristics.

4 Drawing Sheets

Genus and species: *Fragaria* x *ananassa* Duch.
Variety denomination: 'A13-26'.

STATEMENT REGARDING FEDERALLY SPONSORED RESEARCH OR DEVELOPMENT

None

BACKGROUND OF THE INVENTION

'A13-26' is a product of a controlled breeding program carried out by the inventor in the Andalucia region of Spain. 'A13-26' was one of several seedlings resulting from an uncontrolled cross made in the year 2013. The seeds resulting from the uncontrolled cross were germinated indoors and the resulting seedling was transplanted to the trial seedling field. 'A13-26' was selected in the Andalucia region of Spain in the year 2014 based on observations of its fruiting characteristics. In 2015, 'A13-26' was asexually propagated by rooting stolons and was expanded to 30 plants which were planted in replicated trials in the Andalucia region of Spain. The plants were observed and evaluated, and the next year they were expanded for further observation and evaluation. The breeders of 'A13-26' have sold the variety commercially under the Trademark name "Calderon WB" or "Calderon Circle R Brand". Contrast is made with 'Splendor' (U.S. Plant Pat. No. 17,864 under BG-959) in reference to color of the fruit; 'A13-26' fruit is lighter in color, red orange and 'Splendor' presents a dark red fruit. 'A13-26' produces fruit larger in size (5-7 cm) versus 'Splendor' variety of medium size fruit (4.5-5.5 cm). Comparison is made with strawberry variety 'BG-4316' (U.S. Plant Pat. No. 23,255) known commercially in Europe as 'Victory'. The plants of 'A13-26' variety produce a yield of 715.21 g per plant while 'BG-4316' presents a higher yield of 810.66 g per plant. The fruit of 'A13-26' has a firmness of 371 in the penetrometer while 'BG-4316' variety has a greater firmness of 414 in the penetrometer. The fruit of 'A13-26' has a sweeter flavor with a brix of 8.1 while 'BG-4316' contains a brix of 7.6. The fruit of the variety 'A13-26' is orange-red and large, expresses good organoleptic characteristics, among which is a good balance between sugars and acidity and high content of Vitamin C which classifies this fruit for its commercial use in premium quality markets. Throughout several generations of asexual propagation, 'A13-26' has been observed to retain its distinctive characteristics and remain true to type.

BRIEF DESCRIPTION OF THE PHOTOGRAPH

Figure 1:
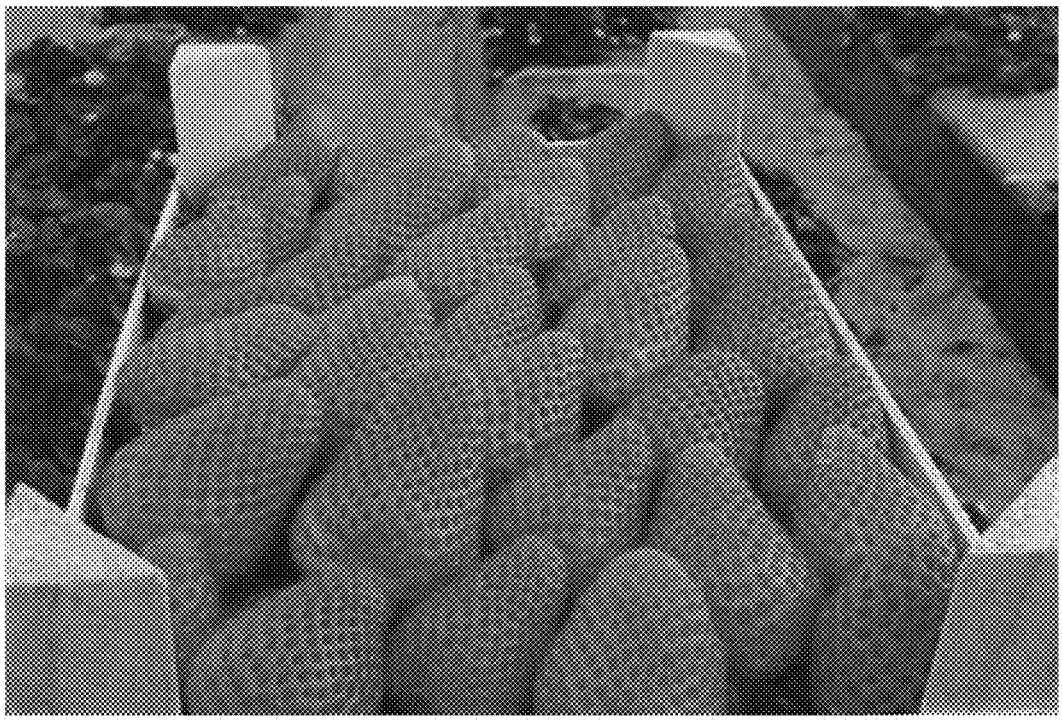
FIG. 1 illustrates mature strawberries of 'A13-26' in a wooden box.
Figure 2:
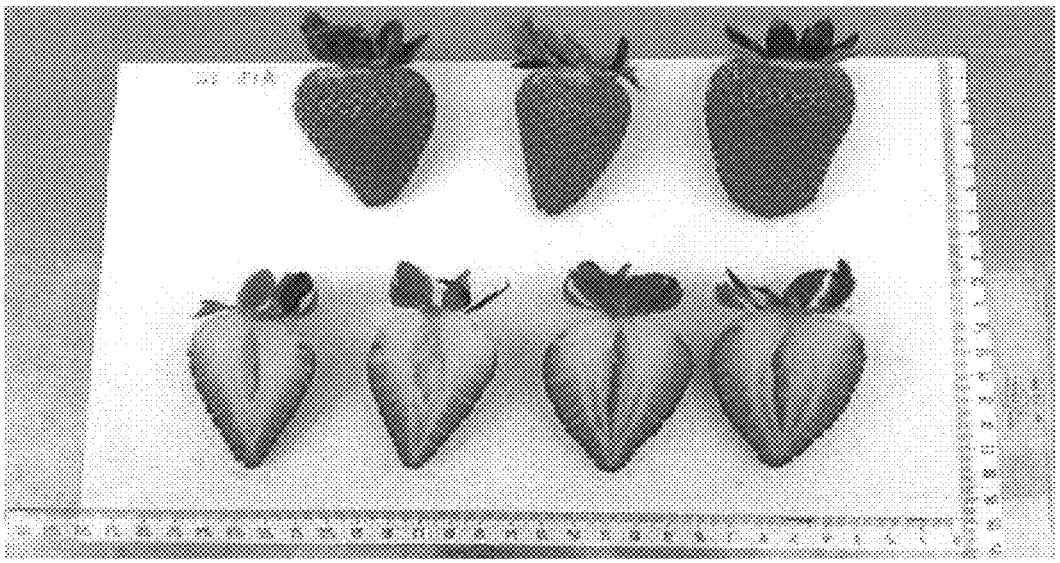
FIG. 2 illustrates individual whole berries and cross sections of whole berries of mature strawberries of 'A13-26'.
Figure 3:
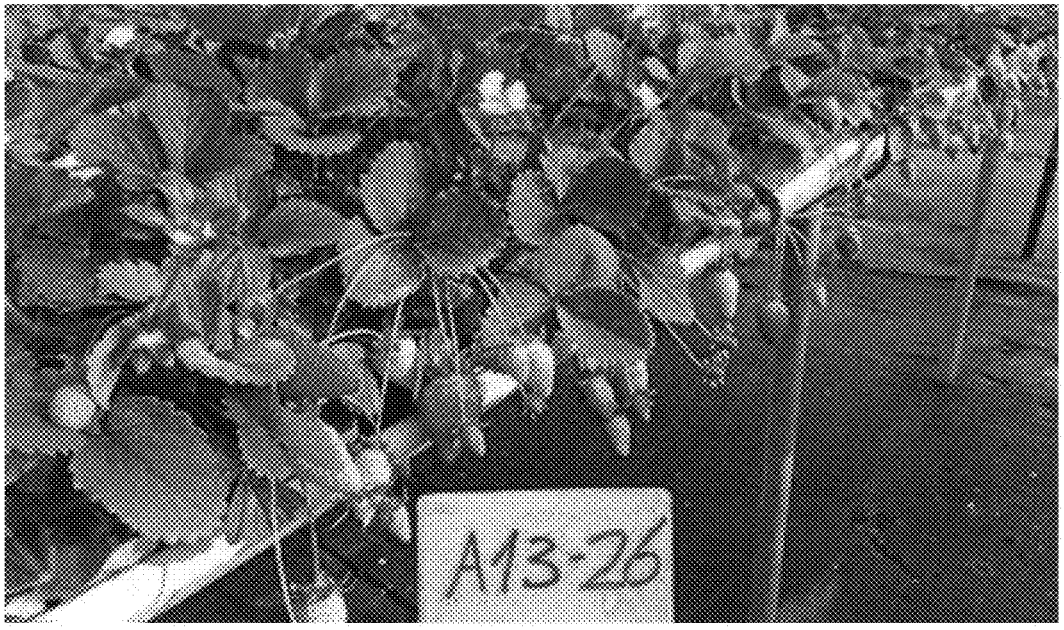
FIG. 3 illustrates 6-month-old plants of 'A13-26' growing in a raised bench system.
Figure 4:
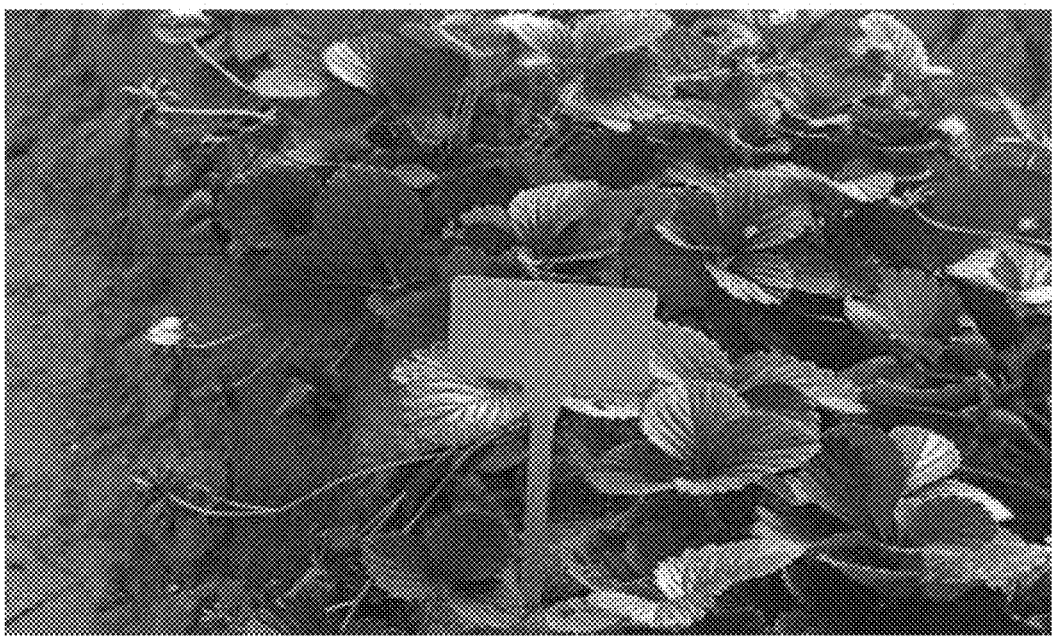
FIG. 4 illustrates immature plants of 'A13-26' growing in a traditional raised bed with black plastic mulch.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is that of a plant age of seven months and is based on observations made during the 2016 and 2017 growing seasons in the Andalucia region of Spain. It should be understood that the characteristics described will vary somewhat depending upon cultural practices and climatic conditions and can vary with location and season. Quantified measurements are expressed as an average of measurements taken from a number of individual plants of the new variety. The measurements of any individual plant or any group of plants, of the new variety may vary from the stated average. Color terminology follows The Royal Horticultural Society Colour Chart, London (R.H.S.) (Sixth Revised Edition, 2015).

General description:

*Ploidy*.—Octoploid.

*Blooming period*.—Approximately January through May in Huelva, Spain.

*Plant average height*.—30 cm.

*Plant average width*.—29 cm.

*Plant type*.—Herbaceous fruit producing perennial.

*Plant habit*.—Upright, semi-compact with dense canopy.

*Cold hardiness*.—Not tested in areas where temperatures of 32° F. occur.

*Root description*.—Fibrous, 10 days to initiate roots, 8 weeks to produce a rooted plant, Greyed-yellow group (160) Light yellow (B).

*Propagation*.—Rooting of stolons.

*Growth rate*.—Vigorous.

*Stem*.—Acaulescent.

Stolons:

*Anthocyanin*.—Variable (absent to moderate).

*Average length*.—30 cm to 40 cm.

*Average diameter*.—4 mm.

*Average number*.—Variable, 30 to 40 stolons.

*Color*.—Yellow-green group (145) Light yellow green (C).

Foliage description:

*Average leaf length*.—11 cm.

*Average leaf width*.—8.5 cm.

*Leaf texture* (*both surfaces*).—Moderately soft.

*Leaf pubescence*.—Medium.

*Leaf division*.—Three leaflets.

*Leaf arrangement*.—Basal.

*Leaf attachment*.—Petiolate.

*Terminal leaflet average length*.—11 cm.

*Terminal leaflet average width*.—8.5 cm.

*Terminal leaflet pubescence density*.—Medium.

*Terminal leaflet texture* (*both surfaces*).—Moderately soft.

*Leaflet shape*.—Broadly ovate to rounded.

*Leaflet margins*.—Serrate, slightly pointed to slightly rounded.

*Leaflet base*.—Asymmetrically oblique and rounded.

*Leaflet apex*.—Round.

*Leaflet venation*.—Pinnate, coloration matched leaflet color.

*Leaflet color*.—Upper surface Green group (138) Moderate yellowish green (A), lower surface Green group (138) Moderate yellow green (C), no variegation present on either surface.

Petiole:

*Petiole*.—Round in shape, strong in strength.

*Average length*.—18 cm.

*Average diameter*.—4 mm.

*Pubescence*.—Low or medium.

*Pubescence density*.—Moderate.

*Pose of hairs*.—Slightly out.

*Texture*.—Moderately soft.

*Anthocyanin*.—Absent.

*Color*.—Yellow-green group (145) Light yellow green (B).

Petiolule:

*Petiolule*.—Round in shape.

*Average length*.—Terminal Leaflets 10 mm, Lateral Leaflets 5 mm.

*Average diameter*.—2 mm.

*Color*.—Yellow-green group (145) Light yellow green (B).

Stipule:

*Average length*.—25 mm.

*Average width*.—12 mm.

*Color*.—Yellow-green group (144) Light yellow green (D).

Flower description:

*Average size* (*diameter*).—41 mm.

*Average number of flowers*.—3 to 6 flowers per cluster.

*Inflorescence*.—Truss.

*Flower initiation and expression conditions*.—Temperature and day-length dependent.

*Time of flowering* (50% *of plants at first flower*).—Early to mid-season.

*Flower fragrance*.—Slight.

Sepal:

*Average length*.—15 mm.

*Average diameter*.—8.7 mm.

*Texture* (*both surfaces*).—Partially soft.

*Color*.—Green group (137) Moderate yellow green (C).

*Sepal position*.—Mixed arrangement relative to the fruit.

Petals:

*Petals*.—Round in shape, obtuse base and apex, slightly overlapping, entire margins.

*Average number*.—5.

*Average length*.—10 mm.

*Average width*.—10.5 mm.

*Texture*.—Soft.

*Color*.—White Group (NN155) White (D).

Peduncle:

*Peduncle*.—Strong in strength.

*Average length*.—35 cm to 45 cm.

*Average diameter*.—4 mm.

*Color*.—Yellow-green group (145) Light yellow green (B).

Pedicel:

*Pedicel*.—Strong in strength.

*Average length*.—7 cm to 10 cm.

*Average diameter*.—2 mm.

*Color*.—Yellow-green group (145) Light yellow green (B).

*Pistils*.—Average of 145, average of 1.1 mm in length, steeply dome shaped, Yellow-green group (151) Strong greenish yellow (C).

*Stigma color*.—Yellow-green group (151) Strong greenish yellow (C).

*Style color*.—Yellow-green group (151) Strong greenish yellow (C).

*Stamens average length*.—1.5 mm.

*Stamens*.—Average of 26, Yellow-green group (151) Strong greenish yellow (B), pollen is moderate in quantity and Vivid Greenish Yellow 2A in color.

*Bracts*.—Observed on the majority of the flower trusses from early developmental stage, which progresses into a typical single leaflet as the truss matures and fruit develops with characteristics similar to leaflets.

Fruit description:

*Shape*.—Primarily conical to cordate with broad shoulders, shape is similar for primary, secondary, and tertiary fruit.

*Season of harvest*.—January through May in Huelva, Spain.

*Time of ripening* (50% *of plants with first ripe fruit*).—Early.

*Time of bearing*.—Short day, Mediterranean.

*Average length of fruit*.—5 cm to 7 cm.

*Average width of fruit*.—3 cm to 5 cm.

*Weight of primary fruit*.—35 g to 50 g.

*Weight of secondary and tertiary fruit*.—15 g to 35 g.

*Fruit cavity*.—Small or medium (4 mm×20 mm).

*Surface*.—Smooth and glossy.

*Glossiness*.—Even and very high.

*External color* (*skin*).—Red group Vivid red (A), color is retained throughout the cropping season and holds up well to high seasonal temperatures.

*Internal color*.—Red group (40) vivid reddish orange (A).

*Evenness of color of skin*.—Even.

*Acidity*.—Low.

*Sweetness*.—High, brix 8.1.

*Firmness*.—Skin is very firm (resistant to bruising), flesh is moderately firm, 371 on penetrometer.

*Juiciness*.—Moderate.

*Aroma*.—High.

*Yield*.—Average of 715.21 g of berries per plant.

*Shelf life*.—An average of 8 to 10 days.

*Achene*.—Orange-red group (31) Strong Yellowish pink (C) on the shady side, Orange-red group (31) strong reddish Orange (B) on the sunny side.

*Achene number*.—An average of 250 per berry.

*Achenes*.—Below the surface.

Disease and pest resistance: 'A13-26' variety is sensitive to the aphid among which *Aphis gossypii* is found. The cultivars of 'A13-26' do not present a high percentage of *Botrytis cinerea*. On the other hand, you have to control the fungus powdery mildew (*Podosphaera aphanis*) that causes the disease of the ash.

What is claimed is:

1. A new and distinct strawberry plant as shown and described herein.

* * * * *